United States Patent [19]

Maryanoff et al.

[11] Patent Number: 4,792,569

[45] Date of Patent: Dec. 20, 1988

[54] ANTICONVULSANT PHENETHYL SULFAMATES

[75] Inventors: Bruce E. Maryanoff, New Hope; Samuel O. Nortey, Lamott, both of Pa.

[73] Assignee: McNeilab, Inc., Spring House, Pa.

[21] Appl. No.: 89,880

[22] Filed: Aug. 27, 1987

[51] Int. Cl.$^4$ .................. A61K 31/255; C07C 143/68
[52] U.S. Cl. ...................... 514/517; 558/48; 558/53
[58] Field of Search .......................... 558/48; 514/517

[56] References Cited

U.S. PATENT DOCUMENTS

| | | | |
|---|---|---|---|
| 3,058,981 | 10/1962 | Avakian et al. | 260/247.2 |
| 3,840,579 | 10/1974 | Fan | 558/48 |
| 4,075,351 | 2/1978 | Hirsch | 424/303 |
| 4,513,006 | 4/1985 | Maryanoff et al. | 514/23 |
| 4,591,601 | 5/1986 | Maryanoff et al. | 514/462 |

OTHER PUBLICATIONS

N. K. Kochetkov et al., in Zhurnal Obshchei Khimii, vol. 41, No. 8, pp. 1866–1871, (1971).
N. K. Kochetkov et al., in Journal of General Chemistry of the USSR 42 (12) 2755–57 (1972).
N. K. Kochetkov et al., in Journal of General Chemistry of the USSR 44(4) 871–875 (1974).
N. K. Kochetkov et al., in Doklady Akademii Nauk SSSR, vol. 216, No. 1, pp. 97–100, (1974).
Tetrahedron Letters No. 36, pp. 3365–3368, Pergamon Press Ltd. (1978) ty T. Tsuchiya.
J. Med. Chem. 1981, 24, 901–903, A. F. Hirsch.
J. Med. Chem. 1987, 30, 880–887, B. E. Maryanoff et al.

*Primary Examiner*—Nicky Chan
*Attorney, Agent, or Firm*—David J. Levy

[57] ABSTRACT

Sulfamates of the following formula (I) are anticonvulsants and are useful in the treatment of epilepsy:

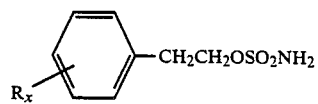

(I)

wherein
R is one or more substituents such as alkyl, halo, alkoxy, $CH_3$ or nitro; and
x is 0–3.

18 Claims, No Drawings

ANTICONVULSANT PHENETHYL SULFAMATES

Sulfamates of various structures are described in references such as N. K. Kochetkov et al in Zhurnal Obshchei Kimii, Vol. 41, No. 8, 1866 to 1871 (1971). Vol. 42, No. 12, 2755 to 2757 (1972) and Vol. 44, No. 4, 871 to 875 (1974) and in Doklady Akademii Nauk SSR, Vol. 216, No. 1, 97 to 100 (1974); T. Tsuchiya et al, in Tetrahedron Letters, No. 36, 3365 to 3368 (1978); A. F. Hirsch in Journal of Medicinal Chemistry, 24, 901 to 903 (1981); and U.S. Pat. No. 4,075,351. Also known are carbamates, including those in U.S. Pat. No. 4,591,601, dioxolane carbamates such as dioxamate as described in U.S. Pat. No. 3,058,981 and topiramate as described in U.S. Pat. No. 4,513,006.

SUMMARY OF THE INVENTION

It has been found that sulfamates of the following formula (I):

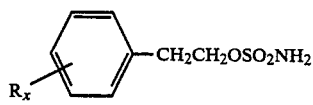

(I)

wherein R is as hereinafter defined, possess anticonvulsant activity in mammals and are thus useful in treating disease states such as epilepsy. Also, because of activity in the inhibition of the enzyme carbonic anhydrase, such compounds are useful in treating glaucoma. Also part of the present invention are pharmaceutical compositions containing one or more sulfamates of formula (I) as well as methods for the treatment e.g., prevention, of convulsions using such compositions.

DETAILED DESCRIPTION OF THE INVENTION

The sulfamates of the invention are of the following formula (I):

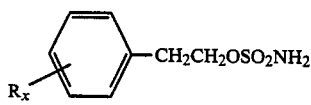

(I)

wherein
R is independently alkyl, halo, alkoxy, $CF_3$ or nitro.
x is 0, 1, 2 or 3.

When x is 2 or 3, R may be the same or different.

R in particular is alkyl of about 1 to 6 carbons, such as methyl, ethyl, iso-propyl, tert-butyl, n-hexyl and n-nonyl. Alkyl throughout this specification includes straight and branched chain alkyl. Halo for R includes chloro, fluoro, bromo and iodo. Alkoxy for R, can be, in particular, of about 1 to 6 carbons such as methoxy, ethoxy, and t-butoxy. The R group can be attached at any of the open phenyl positions, e.g. the 2, 3 or 4 position if x is 1, the 2, 3: 2,4; 2,5; 2,6; 3,4; or 3–5 position if x is 2; and the 2,3,4; 2,3,5; 2,3,6; 2,4,5; 2,4,6; and 3,4,5 position of x is 3.

The compounds of formula (I) may be synthesized by the following methods:
(a) Reaction of an alcohol of the following formula (II):

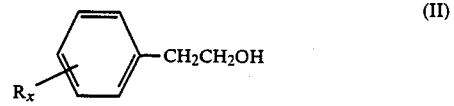

(II)

with chlorosulfamate of the formula $ClSO_2NH_2$ in the presence of a base such as potassium t-butoxide or sodium hydride at a temperature of about $-20°$ to $25°$ C. and in a solvent such as toluene, THF or dimethylformamide.

(b) Reaction of an alcohol of the formula (II) above with sulfurylchloride of the formula $SO_2Cl_2$ in the presence of a base such as triethylamine or pyridine at a temperature of about $-40°$ to $25°$ C. in a solvent such as diethyl ether or methylene chloride to produce a chlorosulfate of the following formula (III):

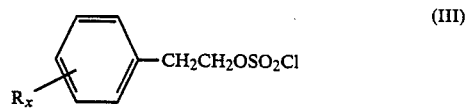

(III)

The chlorosulfate of the formula (III) may then be reacted with ammonia at a temperature of about $-40°$ to $25°$ C. in a solvent such as methylene chloride, THF, $Et_2O$ or acetonitrile to produce a compound of formula (I). The reaction conditions for process (b) are also described by T. Tsuchiya et al. in Tet. Letters, No. 36, pages 3365 to 3368 (1978).

(c) Reaction of the chlorosulfate (III) with a metal azide such as sodium azide in a solvent such as methylene chloride or acetonitrile yields as azidosulfate of the following formula (IV):

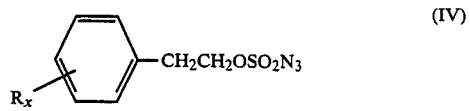

(IV)

as described by M. Hedayatullah in Tet. Lett. p. 2455-2458 (1975). The azidosulfate is then reduced to a compound of formula (I) by catalytic hydrogenation, e.g. with a noble metal and $H_2$ or by heating with copper metal in a solvent such as methanol.

The starting materials of formula (II) may be obtained commercially or by techniques known to those skilled in the art of organic chemistry. The compounds of the invention include the various individual isomers as well as the racemates thereof, e.g., isomerism resulting from branching in the R groups. Also included within the scope of the compounds of formula (I) of this invention are various hydrates and solvates. As used herein, "independently" for R denotes substitutions which are not necessarily the same, e.g. 3-chloro-4-fluoro.

The compounds of formula (I) are useful as anticonvulsant agents. The anticonvulsant activity of the subject compounds was determined using a standard "maximal electroshock test" (MES). In this test, activity is indicated by a block of the tonic extensor seizure caused by application of an electric shock to mice via corneal electrodes, as described by Swinyard et al. in J. Pharmacol. Exptl. Therap. 106, 319 (1952). A more recent description of current anticonvulsant drug screening is given in Swinyard et al. in Epilepsia 19, 409 (1978).

Non-fasted male albino mice of the Swiss Webster strain (Royal-Hart Laboratories, New Hampton, N.Y.) weighing 18-24 grams were used in this test. Six to eight groups of ten mice each were used per $ED_{50}$ determination. The test compounds were administered as aqueous solutions or suspensions prepared with Tween 80 and water. Testing was conducted at 30 minutes following intraperitoneal injection and at 60 minutes following oral administration of the test compound. A group of ten mice injected with saline 10 ml/kg i.p. and tested 30 minutes later served as controls. $ED_{50}$'s were calculated using a computerized probit analysis procedure.

The anticonvulsant activity of compounds of this invention tested according to the Swinyard (1952) method is shown in the following Table I:

TABLE I

| Example | Compound Rx | MES Test % Inhibition | |
|---|---|---|---|
| | | 100 mg/kg 30 min i.p. | 200 mg/kg 60 min p.o |
| 1b | x = 0 | 90% | 100% |
| 2 | 3-$CF_3$ x = 1 | 70% | 100% |
| 3 | 3,4-di$OCH_3$ x = 2 | 30% at 500 mg/kg i.p. in 30 min | |
| 5 | 2-$CH_3$ x = 1 | 90% | 70% |
| 6 | 3-$NO_2$ x = 1 | 80% | 40% |

For treating epilepsy, a compound of formula (I) may be employed at a daily dosage in the range of about 30 to 2000 mg, usually in 2 to 4 divided doses, for an average adult human. A unit dose would contain about 10 to 500 mg of the active ingredient.

In general, compounds of formula (I) may be used in treating epilepsy in a manner similar to that used for phenytoin or topiramate. Medical aspects of the treatment of epilepsy are described by L. S. Goodman et al. in "The Pharmacological Basis of Therapeutics", 5th Ed. pages 201 to 226, Macmillan (1975).

Further, compounds of formula (I) would be expected to be inhibitors of carbonic anhydrase, as determined by the methods described by S. J. Dodgson et al. in the Proc. Natl. Acad. Sci., U.S., 77, pages 5562 to 5566 (1980) or by N. Itada et al. in the Journal Biol. Chem., 252, pages 3881 to 3890 (1977) and as such, are useful in the treatment of glaucoma. The relationship between the treatment of glaucoma and carbonic anhydrase inhibition is described by A. Stein et al in the American Journal of Opthalmology, 95:222-228 (1983). For the treatment of glaucoma, a compound of formula (I) may be administered systemically, e.g. by oral or parenteral routes as described below, or topically in the eye in a mineral oil solution or suspension, or aqueous suspension. When used systemically, the compound would be administered in an amount of about 50 to 500 mg per day for an average adult human, while the topical dosage would be about 1 to 3 drops (per eye) of a solution or suspension containing about 1 to 5% by weight of a compound of formula (I) with the dosage being administered about 1 to 4 times per day.

To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful, suppository and the like, from about 10 to about 500 mg of the active ingredient.

The foregoing compositions are particularly suitable for use in the treatment of epilepsy or the symptoms of epilepsy by a method comprising internally administering to a subject suffering from the symptoms of epilepsy compositions comprising an effective epilepsy inhibiting amount of a compound of formula (I).

Also part of the present invention are intermediates of the formulae (III) and (IV).

In the following Examples and throughout the specification the following abbreviations may be used: g (grams); ml(milliliters); min (minutes); hr (hours); mol (moles); cm (centimeters); v/v (volume to volume); i.p. (intraperitoneally); p.o. (per os, orally); mg/kg (milligrams per kilogram of body weight); mp (melting point); TLC (thin layer chromatography); HPLC (high pressure liquid chromatography); NMR (nuclear magnetic resonance); IR (infrared); DMF (dimethylformamide); THF (tetrahydrofuran); $Et_2O$ (diethylether); EtOAc (ethyl acetate); and C, H, N, etc. (the chemical symbols for the elements).

EXAMPLE 1 a. Sulfamoyl Chloride

Sulfamoyl chloride is prepared by the method described by R. Appel and G. Berger in Chem. Ber., Vol. 91, page 1339-41 (1958) from chlorosulfonyl isocyanate (Aldrich) and formic acid.

b. Phenethylsulfamate

A mixture of 10.0 g (0.08 mole) of phenethyl alcohol in 10 ml DMF was added dropwise to a suspension of sodium hydride (4.8 g, 50% in oil; 0.10 mole) in 30 ml DMF at 0°-5° C. The suspension was stirred for 20 min under argon after which sulfamoyl chloride (12.26 g, 0.10 mole) was added portion wise at 0°-5° C. After stirring for 20 min, the resultant suspension was poured into ice and extracted twice with $Et_2O$. The combined organic phases were washed with saturated brine, dried over potassium carbonate and concentrated in vacuo to give a syrup which was distilled (Kugelrohr) at 80° C.

(0.07 mm of Hg) to give 11.3 g (70.2%) of a colorless syrup.

Elemental Analysis: Calculated for $C_8H_{11}NO_3S$: C, 47.75; H, 5.51; N, 6.96. Found: C, 47.75; H, 5.52; N, 6.93.

EXAMPLE 2

3-(Trifluoromethyl)phenethylsulfamate

A mixture of 4 g (0.02 mole) of 3-(trifluoromethyl)phenethyl alcohol in 10 ml DMF was added dropwise to a suspension of sodium hydride (1.10 g, 60% in oil; 0.08 mole) in 35 ml DMF at 0°–5° C. The suspension was stirred for 20 min under argon after which sulfamoyl chloride (2.8 g, 0.02 mole) was added portionwise at 0°–5° C. After stirring for 20 min, the resultant suspension was poured into ice and extracted twice with $Et_2O$. The combined organic phases were washed with saturated brine, dried over potassium carbonate and concentrated in vacuo to a white solid which was recrystallized in EtOAc/hexane to give 2.58 g (48%) of (trifluoromethyl)phenethyl sulfamate compound, mp 102°–103° C.

Elemental Analysis: Calculated for $C_9H_{10}F_3NO_3S$: C, 40.37; H, 3.73; N, 5.18. Found: C, 40.23; H, 3.75; N, 5.18.

EXAMPLE 3

3,4-Dimethoxyphenethyl sulfamate

A mixture of 5.0 g (0.027 mole) of 3,4-dimethoxy phenethyl alcohol in 12 ml DMF was added dropwise to a suspension of sodium hydride (1.20 g, 60% in oil; 0.09 mole) in 40 ml DMF at 0°–5° C. The suspension was stirred for 20 min under argon after which sulfamoyl chloride (3.54 g, 0.03 mole) was added portionwise at 0°–5° C. After stirring for 20 min the resultant suspension was poured into ice and extracted twice with $Et_2O$. The combined organic phases were washed with saturated brine, dried over potassium carbonate and concentrated in vacuo to a white solid which was recrystallized in EtOAc/hexane to give 0.95 g (13%) of the title compound as a solid, mp 106°–108° C. Both $^{13}C$ and $^1H$ NMR in $CDCl_3$ confirmed the structure.

EXAMPLE 4

4-Bromophenethyl sulfamate

A mixture of 2.95 g (0.015 mole) of 4-bromophenethyl alcohol in 10 ml DMF was added dropwise to a suspension of sodium hydride 0.90 g, 60% in oil; 0.065 mole) in 35 ml DMF at 0°–5° C. The suspension was stirred for 20 min under argon after which sulfamoyl chloride (2.09 g, 0.018 mole) was added portionwise at 0°–5° C. After stirring for 20 min, the resultant suspension was poured into ice and extracted twice with $Et_2O$. The combined organic phases were washed with saturated brine, dried over potassium carbonate and concentrated in vacuo to a white solid which was recrystallized in EtOAc/hexane to give 2.40 g (59%) of the title compound as a white solid, mf 109°–110° C.

Elemental Analysis: Calculated for $C_8H_{10}B_2NO_3S$: C, 34.30; H, 3.60; N, 5.00. Found: C, 34.54; H, 3.61; N, 4.99.

EXAMPLE 5

2-Methylphenethyl sulfamate

A mixture of 2.65 g (0.019 mole) of 2-methylphenethyl alcohol in 10 ml DMF was added dropwise to a suspension of sodium hydride (1.1 g, 60% in oil; 0.08 mole) in 35 ml DMF at 0°–5° C. The suspension was stirred for 20 min under argon after which sulfamoyl chloride (2.86 g, 0.02 mole) was added portionwise at 0°–5° C. After stirring for 20 min the resultant suspension was poured into ice and extracted twice with $Et_2O$. The combined organic phases were washed with saturated brine, dried over potassium carbonate and concentrated in vacuo to a syrup which was purified by preparative HPLC with hexane/EtOAc (1:1, v/v) as the eluant to give 1.76 g (43%) of the title compound as a solid, mp 50°–52° C.

Elemental Analysis: Calculated for $C_9H_{13}NO_3S$: C, 50.22; H, 6.09; N, 6.51. Found: C, 50.40; H, 6.14; N, 6.43.

EXAMPLE 6

3-Nitrophenethylsulfamate

A mixture of (0.02 mole) of 2-nitrophenethyl alcohol in 10 ml DMF was added dropwise to a suspension of sodium hydride (1.10 g, 60% in oil; 0.08 mole) in 35 ml DMF at 0°–5° C. The suspension was stirred for 20 min under argon after which sulfamoyl chloride (2.86, 0.02 mole) was added portionwise at 0°–5° C. After stirring for 20 min the resultant suspension was poured into ice and extracted twice with $Et_2O$. The combined organic phases were washed with saturated brine, dried over potassium carbonate and concentrated in vacuo to a yellow solid; which was recrystallized in EtOAc/hexane to give 3.92 g (79%) of 3-nitrophenethyl sulfamate compound as a yellow solid, mp 113°–114° C.

Elemental Analysis: Calculated for $C_8H_{10}N_2O_5S$: C, 39.02; H, 4.09; N, 11.38. Found: C, 38.99; H, 4.14; N, 11.35.

What is claimed is:

1. A sulfamate of the following formula (I):

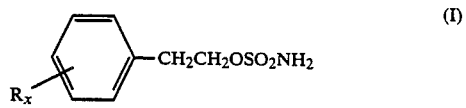

(I)

wherein,

R is independently alkyl, halo, alkoxy, $CF_3$ or nitro; and x is 0, 1, 2 or 3.

2. The sulfamate of claim 1, wherein for R said alkyl is of about 1 to 6 carbons, said halo is chloro, fluoro, bromo or iodo and said alkoxy is of about 1 to 6 carbons.

3. The sulfamate of claim 1, wherein x is 0.

4. The sulfamate of claim 1, wherein x is 1.

5. The sulfamate of claim 1, wherein x is 2.

6. The sulfamate of claim 1, wherein x is 3.

7. The sulfamate of claim 1, wherein R is $CF_3$, methoxy, bromo, methyl or nitro.

8. The sulfamate of claim 1, wherein x is 0 or x is 1 with R being $CF_3$ or methyl.

9. The sulfamate of claim 1, wherein said sulfamate is: phenethyl sulfamate;
3-(trifluoromethyl)phenethyl sulfamate;
3,4-dimethoxyphenethyl sulfamate;
4-bromophenethyl sulfamate;
2-methylphenethyl sulfamate; or
3-nitrophenethyl sulfamate.

10. A pharmaceutical composition for the treatment of convulsions comprising an anti-convulsion effective amount of a sulfamate of claim 1 and a pharmaceutically-acceptable carrier.

11. The pharmaceutical composition of claim 10, wherein said sulfamate is present in a unit dosage amount of about 10 to 500 milligrams of the sulfamate.

12. A method for the treatment of convulsions in a mammal which comprises administering to the mammal, an anti-convulsion effective amount of the pharmaceutical composition of claim 10.

13. The sulfamate of claim 1, wherein said sulfamate is phenethyl sulfamate.

14. The sulfamate of claim 1, wherein said sulfamate is 3-(trifluoromethyl)phenethyl sulfamate.

15. The sulfamate of claim 1, wherein said sulfamate is 3,4-dimethoxyphenethyl sulfamate.

16. The sulfamate of claim 1, wherein said sulfamate is 4-bromophenethyl sulfamate.

17. The sulfamate of claim 1, wherein said sulfamate is 2-methylphenethyl sulfamate.

18. The sulfamate of claim 1, wherein said sulfamate is 3-nitrophenethyl sulfamate.

* * * * *